(12) United States Patent
Harder et al.

(10) Patent No.: US 6,252,137 B1
(45) Date of Patent: Jun. 26, 2001

(54) **SOYBEAN HOMOLOG OF SEED-SPECIFIC TRANSCRIPTION ACTIVATOR FROM *PHASEOLUS VULGARIS***

(75) Inventors: Patricia A. Harder, Wilmington, DE (US); Joan T. Odell, Unionville, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/185,160

(22) Filed: Nov. 3, 1998

Related U.S. Application Data
(60) Provisional application No. 60/065,459, filed on Nov. 12, 1997.

(51) Int. Cl.$^7$ .............................. C12N 5/04; C12N 15/29; C12N 15/82; C12N 15/90; A01H 5/00
(52) U.S. Cl. ........................ 800/278; 435/320.1; 435/419; 435/468; 536/23.6; 800/298
(58) Field of Search ................................ 435/69.1, 320.1, 435/410, 415, 419, 468; 536/23.6; 800/278, 295, 298, 312

(56) References Cited

FOREIGN PATENT DOCUMENTS

| | | | |
|---|---|---|---|
| 0 242 236 | 10/1987 | (GB) | .............................. C12N/15/00 |
| 0 571 741 | 12/1993 | (GB) | .............................. C12N/15/82 |
| 2 307 477 | 5/1997 | (GB) | .............................. C12N/15/11 |

OTHER PUBLICATIONS

Li et al, Proc. Natl. Acad. Sci., USA, vol. 96, pp. 7104–7109, 1999.*
Bobb et al., Embl Sequence Database, Nov. 10, 1995, XP002101501.
Giraudat et al. (1992) Plant Cell 4:1251–1261.
McCarty et al. (1991) Cell 66:895–905.
Hattori et al. (1994) Plant Molecular Biology 24:805–810.
Bobb et al. (1997) Nucleic Acids Rec. 25:641–647.
Nambara et al. (1994) Plant Cell Physiol. 35:509–513.
Parcy et al. (1994) Plant Cell 6:1567–1582.
Kriz et al. (1990) Plant Physiol. 92:538–542.
NCBI General Identifier No. AAA87030.
Plant J. 8(3), 331–343 (1995).
Chu et al., (1975) Sci. Sin. Peking 18:659–668.
Odell et al. (1985) Nature 313:810–812.
Klein et al., (1987) Nature 327:70–73.
Fromm et al., (1990) Bio/Technology 8:833–839.
Doyle et al. (1986) J. Biol. Chem. 261:9228–9238.
Gritz et al. (1983) Gene 25:179–188.

* cited by examiner

*Primary Examiner*—Paula Hutzell
*Assistant Examiner*—Ashwin D. Mehta

(57) ABSTRACT

This invention relates to isolated nucleic acid fragments encoding all or a substantial portion of a soybean homolog of the *Phaseolus vulgaris* PvAlf transcription activator. The invention also relates to the construction of chimeric genes encoding all or a portion of a soybean homolog of the *Phaseolus vulgaris* PvAlf transcription activator, in sense or antisense orientation, wherein expression of the chimeric gene results in production of altered levels of a plant homolog of the *Phaseolus vulgaris* PvAlf transcription activator in a transformed host cell. The invention also relates to targeting of the soybean homolog of the *Phaseolus vulgaris* PvAlf transcription activator to a novel promoter region by the addition of either a DNA-binding domain or a protein-protein interaction domain, thus leading to a higher level of gene expression.

9 Claims, 3 Drawing Sheets

```
              541                                                          600
sbs20.PRO     ............................................................
sbs12.PRO     NTALAAPHIRNESR.NRTNQQARIGGAAGELAPVIPAERPVVQPVVDRSAMGTQNCHQNR
sb8a.PRO      TTGLAAPHIRNPTA.NRTNQANTGGAAGELAR..PAERPPA....VDRSALGTQNCRQSP
03d6.PRO      NTALAAPHIRNESR.NRTNQQAMIGGAAGELAPVIPAERPVVQPVVDRSAMGTQNCPPNL
pvalf.PRO     TTGLVAPHQPNSAAANRTNQANTGGPASELAPVVEADRLAGQTVVDRTTMHTQNSHQNR 601                                                          660
sbs20.PRO     ............................................................
sbs12.PRO     VASDRRQGNRPERNLRELLGRVLRQSDVGLLGKIVLPRELAETHLPELEARQGISTMED
sb8a.PRO      VASDRRQGNRPEENLRELLQNVLRQSDVSSLGRIVLEKKDARTHLPQLSARYGISTMEH
03d6.PRO      IASDRRQGNRPEKNLRELLQRVIKQSDVGSLGRIVLDPKRBACTHLPELSARQGISTMED
pvalf.PRO     AASDRRQGNRPEAQVRELLGDKVERQSDVGKLGRIVLDPKRENETHLPELSARTGISTMED 661                                                          720
sbs20.PRO     ............................................................
sbs12.PRO     IGTSLYWNMPEYRNWPRNESRQYLLENTGDEVRANGLQEGDETVYSDVEGGKYMIRGVKV
sb8a.PRO      IGTSPISMMFYIWPNNIKHMYLLEKTGDEWRANGLQEGDFTVVYSDVEGGKYMLPSVKV
03d6.PRO      IGTSRYWNMPFYRQWPNNKSRQYLLENTGDEVRANGLQEGDETVYSDVEGGKYMIRGVKV
pvalf.PRO     IGTSRYWNMPEFRNWPRNESRQYMRENTGDEERANGLQEGDETVYSDVEGGKYMIRGVKV 721                                                          774
sbs20.PRO     ..........................................................K
sbs12.PRO     RQQGVREPTKQGFSQRNQRGTGTNASSTAGTAANDGTSSGRKTSEKSSILI
sb8a.PRO      RQQGVREPTKSVKASDNQRGTGTNASSTAGTAANDKTPSGRKRAEKSSELI
03d6.PRO      RQQGVKEPTKQGCKSQDNQREIGTNASSTAGTAANDGTSSGRKTSERSGLI
pvalf.PRO     RQQGVREPTKSPDGRSQRT..TRGTNASYTAGTAANKMSGHRN..........
```

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

```
GGCTCCTCTC ATGGTGCCTC CACAGCAATT TCCACAACCC ATGGTTGGGT ATGTGGGTGA      60

CCCTTACACT AGTGGTGCTG CTTCAAATAA CATATCAGCC ACTCATAACC ATAACAACAG     120

CAACCCTTAT CAACCTGGTG CAGAACAATA CCACATGTTG GAGTCAGCAC ATTCATGGCC     180

ACATTCTCTG TTCAATGTTG CTTCTAACTA TAGTCAGTCT TTTGGGGACA ATAATGGTCT     240

TAACCCACAT GGGGGTTTCG GTGGTGGAGG CTATGGCAAT AACCAGTACC CTTATCAGTT     300

TTTTCATGGC CCTGGTGATA GTTGATGAGT TGGGCCCTCC GCGACGAAGG AACGAGGAAA     360

AAAATGGNAG GCAAAAGGNT TTNTCCAA                                        388
```

(2) INFORMATION FOR SEQ ID NO: 2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 2:

```
CATGTGGGTT AAGACCATT                                                   19
```

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 3:

AATTAACCCT CACTAAAGGG                                                    20

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 4:

GTTCTGTCTC ATCACAGGAA T                                                  21

(2) INFORMATION FOR SEQ ID NO: 5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 5:

TAATACGACT CATATAGGG                                                     19

(2) INFORMATION FOR SEQ ID NO: 6:

(i) SEQUENCE CHARACTERISTICS:
        (A) LENGTH: 899 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

AAAATCTATC TTCCCAGAAC AAACCAAGGG TGTCTCTGAA ATTGTCATGT CCACGTTAAG         60

GTCTTGATTG GCTTTCTGGG TTTGAGAAG AATCTCTGCT TCACTCTCTT CACTGCTGTG         120

GGAGGTAACT GACCCAAACC CTATTGGTTT TGGCAACATG GAAGATGAAC ACACTTTGGC        180

GGTTGCTGAG AGAGAGATGT GGCTGAACAG TGACCAAGAC GAGTTCCTAG GTGTCAATGA        240

TGCTTCCATG TTCTACGCTG ATTTCCCTCC TCTCCCTGAT TTCCCTTGCA TGTCATCATC        300

ATCATCTTCA TCTTCAGCAA CACCACTTCC CGTGAAAACC ATGACATGTT CCACCACCAC        360

CACCACTTCC TCTTCTTCCT CTTCCTCTTC TTGGGCCATT TTGAAGTCAG ATGCTGAGGA        420

AGATGCAAAA AAAACCATT GCAACCGATA CATGCATGAC CAACTTGATG CAATTTGCCT         480

TCCTTCCACC GCTTCCATGG AATATCCCCA ACAGCAAAAC CCTGATCCTG GCCTTGGTGG        540

CACTGTTGGA GAGTGCATGG AGGATGTTAT GGACACTTTT GGTTACATGG AGCTTTTGGA       600

GGCCAATGAT TTCTTCGACC CTGCCTCTAT CTTTCAGAAC GAGGAAAACG AAAACCCTTT       660

ATTGGAGTTT GGCACACTGG AGGAGCATGT GCCGTTTCAT GAAGAGCAAC ATGCAATGGT       720

```
GCATCATCAG CAAGGCAAGC AAGCAGAAGA GGATCATCAG GTCCCTTTTT GTGAAGAGAT    780

CCAAGGAGAT GAAGAAGGTG GTGATGGTGT TGGAGTAAGT GATGAGATGA TCAATGTGTT    840

TTTGGAGTGG TTAAAGTCTA ACAAGGATAG TGTCTCAGCT AATGACTTGA AGAAATGAG     899
```

(2) INFORMATION FOR SEQ ID NO: 7:

(i) SEQUENCE CHARACTERISTICS:
        (A) LENGTH: 246 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 7:

```
Met Glu Asp Glu His Thr Leu Ala Val Ala Glu Arg Glu Met Trp Leu
  1               5                  10                  15

Asn Ser Asp Gln Asp Glu Phe Leu Gly Val Asn Asp Ala Ser Met Phe
                 20                  25                  30

Tyr Ala Asp Phe Pro Pro Leu Pro Asp Phe Pro Cys Met Ser Ser Ser
             35                  40                  45

Ser Ser Ser Ser Ser Ala Thr Pro Leu Pro Val Lys Thr Met Thr Cys
 50                  55                  60

Ser Thr Thr Thr Thr Thr Ser Ser Ser Ser Ser Ser Ser Ser Trp Ala
 65                  70                  75                  80

Ile Leu Lys Ser Asp Ala Glu Asp Ala Lys Lys Asn His Cys Asn
                 85                  90                  95

Arg Tyr Met His Asp Gln Leu Asp Ala Ile Cys Leu Pro Ser Thr Ala
                100                 105                 110

Ser Met Glu Tyr Pro Gln Gln Gln Asn Pro Asp Pro Gly Leu Gly Gly
                115                 120                 125

Thr Val Gly Glu Cys Met Glu Asp Val Met Asp Thr Phe Gly Tyr Met
            130                 135                 140

Glu Leu Leu Glu Ala Asn Asp Phe Phe Asp Pro Ala Ser Ile Phe Gln
145                 150                 155                 160

Asn Glu Glu Asn Glu Asn Pro Leu Leu Glu Phe Gly Thr Leu Glu Glu
                165                 170                 175

His Val Pro Phe His Glu Glu Gln His Ala Met Val His His Gln Gln
                180                 185                 190

Gly Lys Gln Ala Glu Glu Asp His Gln Val Pro Phe Cys Glu Glu Ile
            195                 200                 205

Gln Gly Asp Glu Glu Gly Gly Asp Gly Val Gly Val Ser Asp Glu Met
            210                 215                 220

Ile Asn Val Phe Leu Glu Trp Leu Lys Ser Asn Lys Asp Ser Val Ser
225                 230                 235                 240

Ala Asn Asp Leu Lys Lys
                245
```

(2) INFORMATION FOR SEQ ID NO: 8:

(i) SEQUENCE CHARACTERISTICS:
        (A) LENGTH: 1048 base pairs
        (B) TYPE: nucleic acid
        (C) STRANDEDNESS: single
        (D) TOPOLOGY: linear (ii) MOLECULE TYPE: cDNA -continued (xi) SEQUENCE DESCRIPTION: SEQ ID NO: 8:

```
CTGTCTCATC ACAGGAATCA TAGTGGTAAT CACCAGAATC AAGGGTCTGA CCCTCATGCA      60
AGAATGGGGG GTGATAATTG CAACACTGCT TTGGCTGCAC CTCATCACGC AAATCCTTCA     120
GCCAATTGGA TGTACTGGCA GGCTATGATT GGCGGCGCGG CAGGTCCTTT GGCTCCGGTG     180
ATTCCGGCCG AGCCGCCGGT GGTACAACCG GTCGTGGACC GGTCGGCCAT GCAGACACAG     240
AATTGTCATC AGAATCGAGT TGCATCAGAT AGGAGACAGG GTTGGAAGCC TGAGAAGAAC     300
TTGAGGTTCC TTCTGCAAAA GGTGTTGAAA CAAAGCGATG TTGGAATTTT GGGGAAAATA     360
GTTTTGCCAA AAAAAGAGGC AGAAACCCAT TTGCCAGAGC TGGAGGCAAG AGATGGAATT     420
TCCATAACAA TGGAAGACAT TGGAACTTCA CTTGTTTGGA ACATGCGCTA TAGATACTGG     480
CCGAACAACA AAAGCAGAAT GTATTTGCTC GAGAACACTG GTGACTTTGT GAGAGCCAAT     540
GGACTCCAAG AGGGAGATTT CATAGTGATA TACTCAGATG TGAAGTGTGG CAAATATATG     600
ATAAGAGGAG TGAAAGTGAG GCAACAAGGT GTGAAACCAG AGACCAAGAA AGCAGGAAAA     660
TCGCAGAAAA ACCAGCATGG GACAGGGACT AATGCATCAA GTACAGCTGG TACTGCTGCT     720
AATAATGGCA CGTCATCGTC ACCGAAAACC AAATCTGAAA AAGTAGTAA ATTAATATAA      780
TATATAGTAT ATGTATGTAC AATATATATT ATGGCATATA TAATAAAATA AGAGACTCTC     840
AAGTCTGAAC ACGGTGCTCA CATATAATGT TGTGAAGTTT GAGCATGCCC TGCAATGGAG     900
GCTGTCAAGG ATTTGTATAA CAGTATTTTG GGTAATACTT CTTTTAGTAG TTTATTTTGC     960
GATTGTTATT AAAAAAAGAA AAAAAAAAC TCGAAGGGGG GCCCGGTACC CAATTCGCCC     1020
TATAGTGAGT CCTTATTAAA CCGAATTC                                       1048
```

(2) INFORMATION FOR SEQ ID NO: 9:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 9:

```
Leu Ser His His Arg Asn His Ser Gly Asn His Gln Asn Gln Gly Ser
1               5                  10                  15

Asp Pro His Ala Arg Met Gly Gly Asp Asn Cys Asn Thr Ala Leu Ala
            20                  25                  30

Ala Pro His His Ala Asn Pro Ser Ala Asn Trp Met Tyr Trp Gln Ala
        35                  40                  45

Met Ile Gly Gly Ala Ala Gly Pro Leu Ala Pro Val Ile Pro Ala Glu
    50                  55                  60

Pro Pro Val Val Gln Pro Val Val Asp Arg Ser Ala Met Gln Thr Gln
65                  70                  75                  80

Asn Cys His Gln Asn Arg Val Ala Ser Asp Arg Arg Gln Gly Trp Lys
                85                  90                  95

Pro Glu Lys Asn Leu Arg Phe Leu Leu Gln Lys Val Leu Lys Gln Ser
            100                 105                 110

Asp Val Gly Ile Leu Gly Lys Ile Val Leu Pro Lys Lys Glu Ala Glu
        115                 120                 125

Thr His Leu Pro Glu Leu Glu Ala Arg Asp Gly Ile Ser Ile Thr Met
    130                 135                 140

Glu Asp Ile Gly Thr Ser Leu Val Trp Asn Met Arg Tyr Arg Tyr Trp
```

```
145                 150                 155                 160
Pro Asn Asn Lys Ser Arg Met Tyr Leu Leu Glu Asn Thr Gly Asp Phe
                165                 170                 175

Val Arg Ala Asn Gly Leu Gln Glu Gly Asp Phe Ile Val Ile Tyr Ser
            180                 185                 190

Asp Val Lys Cys Gly Lys Tyr Met Ile Arg Gly Val Lys Val Arg Gln
                195                 200                 205

Gln Gly Val Lys Pro Glu Thr Lys Lys Ala Gly Lys Ser Gln Lys Asn
            210                 215                 220

Gln His Gly Thr Gly Thr Asn Ala Ser Ser Thr Ala Gly Thr Ala Ala
225                 230                 235                 240

Asn Asn Gly Thr Ser Ser Ser Pro Lys Thr Lys Ser Glu Lys Ser Ser
                245                 250                 255

Lys Leu Ile
```

(2) INFORMATION FOR SEQ ID NO: 10:

(i) SEQUENCE CHARACTERISTICS:
        (A) LENGTH: 2517 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
TGCATGCAGG GGTGGTAACT GAGCCAAACC CTATTGGTTT TGGCACCATG GAAAACGAAC     60
ACACTTTGGC GGTTGCTGAG AGAGAGATGT GGCTGAACAG TGACCAAGAC GAGTTCCTAG    120
GAGTCAATGA TGCTTCCATG TTCTACGCCG ATTTCCCTCC TCTCCCTGAT TTCCCTTGCA    180
TGTCATCATC ATCATCTTCT TCTTCAGCAC TACCATTTCC TGTGAAGACC ATGACATGTT    240
CCACCAGAAC CACAACAACA ACCACCACTT CCTCTTCTTC CTCTTCCTCA TCCTGGGCCG    300
TGTTGAAGTC AGATGCTGAG GAAGATGCAG AGAAAAATCA TTGCAACCGC TACATGCATG    360
ACCAACTTGA TGCTACTTTG TCTTCCACTG CTTCCATGGA AGTTTCTCAA CAAAAAAACC    420
TCGATCCTGG GCTTGGTGGC CCTGTTGGTG AGTGCATGGA TGATGTTATG GACACTTTTG    480
GGTACATGGA GCTTTTGGAG GCCAATGATT TCTTCGACCC TGCCTCTATC TTTCAGAACG    540
AGGATAACGA AAACCCTTTA GTAGATTTCG GCACACTGGA GCAGCATGTG CCGTTGCATG    600
ATGAGCAACA TGAAATGTTG CATCATCAGC AAGGGAGAAC AGAAGAGGTT GATCATCAGG    660
TTCCTGTGTG TGAAGAGATC CAAGGAGATG AAGAAGGTGG TGATGGTGTT GGAGTAGACG    720
ATGAGATGAG TAATGTGTTC TTGGAGTGGC TCAAGTCTAA CAAGGATAGT GTCTCTGCTA    780
ATGATTTGAG GAATGTGAAG CTCAAGAAGG CGACGATTGA AAGTGCTGCG AGGCGGCTAG    840
GGGGAGGAAA AGAAGCCATG AAGCAGTTGC TGAAGCTGAT TCTTGAGTGG GTTCAAACCA    900
GCCATCTTCA GAATAAGCGG CGTAAGGAGA ATAACGGTAG CAGTATTAGC AGTGCACTTC    960
AGGCACAGTT TCCGGATCGT AGTGTCCAGA CAACCAGAA TACACAAAGT GGTTCATTTT   1020
CACCTGAATC AAACGCTTGT TTCAACAACC AGACACCGTG GTTGAGTCCT CAAACTTTTG   1080
CAACAGATCA GGCTCCTCTC ATGGTGCATC CACAGCAATT TCAACAACCC ATGGTTGGGT   1140
ATGTGGGTGA CCCTTACACT AGTGGTGCTG CTTCAAATAA CATAACAACT TCTCATAATC   1200
ATAACAGCAA CAACCCCTAT CAACCTGGTG CAGAACAATA TCACATGTTG GAGTCGGCAC   1260
ATTCATGGCC TCATTCTCAG TTCAATGTTG CTTGTCACTA TAACCAGTCT TTTGGGGACA   1320
```

-continued

```
ATAATGGTAT TTCCCCACAT GGGGGTTTTG GTGGTGGCTA TGGCAATAAC CATTACCCTT    1380

ACCAGTTTTT TCATGGCCCT GGTGATACGT TGATGAGGTT GGGTCTCTCG GCGACGAAGG    1440

AAGCGAGGAA GAAGAGAATG GCGAGGCAGA GAAAGTTTCT GTCTCATCAC AGGCATCATA    1500

ATGGTATTTA CCAGAATCAG GGTTCACACC CACATGCAAG ATTGGGGGGT GGTGATAATA    1560

GCACCACTGG TTTGGCTGCA CCTCATCATG CAAATCCTAC AGCCAATTGG ATGTACTGGC    1620

AGGCTATGAC GGGCGGTGCG GCGGGTCCTT TGGCTCCCCC GGCCGAACCG CCAGCTGTGG    1680

ACCGGTCTGC CTTGCAGACA CAGAATTGTC ATCAGAGTCC AGTTGCATCA GATAGGAGAC    1740

AGGGTTGGAA GCCTGAGAAA AACTTGAGGT TCCTTCTGCA GAACGTGTTG AAACAAAGCG    1800

ATGTGGGAAG TTTGGGGAGA ATAGTTTTGC CAAAAAAGA CGCAGAAACC CATTTGCCAC     1860

AGCTGGAGGC CAGATATGGA ATTTCCATAA CAATGGAACA CATTGGAACT TCGCCCATTT    1920

CTAACATGCG CTATATATAC TGGCCGAACA ACATAAAACA TATGTATTTG CTCGAGAAAA    1980

CTGGTGACTT TTGGAGAGCC AATGGACTCC AAGAGGGAGA TTTCATAGTG ATATACTCAG    2040

ATGTGAAGTG TGGCAAATAT ATGATAAGAG GAGTGAAAGT GAGGCAACAA GGTGTGAAAC    2100

CAGAGACCAA GAAAGTAGGA AAATCGCAGA AAACCAGCA TGGGACAGGG ACAAATGCAT     2160

CAACTACAGC TTGTACTGCT GCTAATAATG GCACGCCATC GTCACCGAAA ACCAAAGCTG    2220

AAAAAAGTAG TAAATTAATA TAATACATAC AATATGTATG TACAATATAT ATTATATTAT    2280

ATTATATATA ATAAAATAAG AGACTCTGAA GTCTGAACAC GGTGCTCCAT AATGTTGTGG    2340

AGTTTTAGCA TGCCCTGCAA TGGACGCTGT CAAGGATTTG TATAACAGTA TTTTGGGTAT    2400

ATTTCTCTTC ATAATTTATT TTGCGATTGT TATGTGAAAA TGTTGTATGT GTTTAACTTG    2460

GATGTACATG TTACGTTATT AGTGGTCTAT GTGATGTTCA TTTAAGACTT GAATTCC       2517
```

(2) INFORMATION FOR SEQ ID NO: 11:

(i) SEQUENCE CHARACTERISTICS:
        (A) LENGTH: 731 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 11:

```
Met Glu Asn Glu His Thr Leu Ala Val Ala Glu Arg Glu Met Trp Leu
1               5                   10                  15

Asn Ser Asp Gln Asp Glu Phe Leu Gly Val Asn Asp Ala Ser Met Phe
            20                  25                  30

Tyr Ala Asp Phe Pro Pro Leu Pro Asp Phe Pro Cys Met Ser Ser Ser
        35                  40                  45

Ser Ser Ser Ser Ser Ala Leu Pro Phe Pro Val Lys Thr Met Thr Cys
    50                  55                  60

Ser Thr Arg Thr Thr Thr Thr Thr Thr Ser Ser Ser Ser Ser Ser Ser
65                  70                  75                  80

Ser Ser Trp Ala Val Leu Lys Ser Asp Ala Glu Asp Ala Glu Lys
            85                  90                  95

Asn His Cys Asn Arg Tyr Met His Asp Gln Leu Asp Ala Thr Leu Ser
            100                 105                 110

Ser Thr Ala Ser Met Glu Val Ser Gln Gln Lys Asn Leu Asp Pro Gly
        115                 120                 125

Leu Gly Gly Pro Val Gly Glu Cys Met Asp Asp Val Met Asp Thr Phe
    130                 135                 140
```

-continued

```
Gly Tyr Met Glu Leu Leu Glu Ala Asn Asp Phe Phe Asp Pro Ala Ser
145                 150                 155                 160

Ile Phe Gln Asn Glu Asp Asn Glu Asn Pro Leu Val Asp Phe Gly Thr
            165                 170                 175

Leu Glu Gln His Val Pro Leu His Asp Glu Gln His Glu Met Leu His
            180                 185                 190

His Gln Gln Gly Arg Thr Glu Val Asp His Gln Val Pro Val Cys
            195                 200                 205

Glu Glu Ile Gln Gly Asp Glu Gly Gly Asp Gly Val Gly Val Asp
    210                 215                 220

Asp Glu Met Ser Asn Val Phe Leu Glu Trp Leu Lys Ser Asn Lys Asp
225                 230                 235                 240

Ser Val Ser Ala Asn Asp Leu Arg Asn Val Lys Leu Lys Lys Ala Thr
            245                 250                 255

Ile Glu Ser Ala Ala Arg Arg Leu Gly Gly Lys Glu Ala Met Lys
            260                 265                 270

Gln Leu Leu Lys Leu Ile Leu Glu Trp Val Gln Thr Ser His Leu Gln
            275                 280                 285

Asn Lys Arg Arg Lys Glu Asn Asn Gly Ser Ser Ile Ser Ser Ala Leu
290                 295                 300

Gln Ala Gln Phe Pro Asp Arg Ser Val Gln Asn Asn Gln Asn Thr Gln
305                 310                 315                 320

Ser Gly Ser Phe Ser Pro Glu Ser Asn Ala Cys Phe Asn Asn Gln Thr
            325                 330                 335

Pro Trp Leu Ser Pro Gln Thr Phe Ala Thr Asp Gln Ala Pro Leu Met
            340                 345                 350

Val His Pro Gln Gln Phe Gln Gln Pro Met Val Gly Tyr Val Gly Asp
            355                 360                 365

Pro Tyr Thr Ser Gly Ala Ala Ser Asn Asn Ile Thr Thr Ser His Asn
            370                 375                 380

His Asn Ser Asn Asn Pro Tyr Gln Pro Gly Ala Glu Gln Tyr His Met
385                 390                 395                 400

Leu Glu Ser Ala His Ser Trp Pro His Ser Gln Phe Asn Val Ala Cys
            405                 410                 415

His Tyr Asn Gln Ser Phe Gly Asp Asn Asn Gly Ile Ser Pro His Gly
            420                 425                 430

Gly Phe Gly Gly Tyr Gly Asn Asn His Tyr Pro Tyr Gln Phe Phe
            435                 440                 445

His Gly Pro Gly Asp Thr Leu Met Arg Leu Gly Leu Ser Ala Thr Lys
450                 455                 460

Glu Ala Arg Lys Lys Arg Met Ala Arg Gln Arg Lys Phe Leu Ser His
465                 470                 475                 480

His Arg His His Asn Gly Ile Tyr Gln Asn Gln Gly Ser His Pro His
            485                 490                 495

Ala Arg Leu Gly Gly Gly Asp Asn Ser Thr Thr Gly Leu Ala Ala Pro
            500                 505                 510

His His Ala Asn Pro Thr Ala Asn Trp Met Tyr Trp Gln Ala Met Thr
            515                 520                 525

Gly Gly Ala Ala Gly Pro Leu Ala Pro Pro Ala Glu Pro Pro Ala Val
            530                 535                 540

Asp Arg Ser Ala Leu Gln Thr Gln Asn Cys His Gln Ser Pro Val Ala
545                 550                 555                 560
```

Ser Asp Arg Arg Gln Gly Trp Lys Pro Glu Lys Asn Leu Arg Phe Leu
            565                 570                 575

Leu Gln Asn Val Leu Lys Gln Ser Asp Val Gly Ser Leu Gly Arg Ile
        580                 585                 590

Val Leu Pro Lys Lys Asp Ala Glu Thr His Leu Pro Gln Leu Glu Ala
        595                 600                 605

Arg Tyr Gly Ile Ser Ile Thr Met Glu His Ile Gly Thr Ser Pro Ile
    610                 615                 620

Ser Asn Met Arg Tyr Ile Tyr Trp Pro Asn Asn Ile Lys His Met Tyr
625                 630                 635                 640

Leu Leu Glu Lys Thr Gly Asp Phe Trp Arg Ala Asn Gly Leu Gln Glu
            645                 650                 655

Gly Asp Phe Ile Val Ile Tyr Ser Asp Val Lys Cys Gly Lys Tyr Met
            660                 665                 670

Ile Arg Gly Val Lys Val Arg Gln Gln Gly Val Lys Pro Glu Thr Lys
            675                 680                 685

Lys Val Gly Lys Ser Gln Lys Asn Gln His Gly Thr Gly Thr Asn Ala
        690                 695                 700

Ser Thr Thr Ala Cys Thr Ala Ala Asn Asn Gly Thr Pro Ser Ser Pro
705                 710                 715                 720

Lys Thr Lys Ala Glu Lys Ser Ser Lys Leu Ile
            725                 730

(2) INFORMATION FOR SEQ ID NO: 12:

(i) SEQUENCE CHARACTERISTICS:
        (A) LENGTH: 2454 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION:SEQ ID NO: 12:

```
GGCACGAGGA CCCAAACCCT ATTGGTTTTG GCAACATGGA AGATGAACAC ACTTTGGCGG      60

TTGCTGAGAG AGAGATGTGG CTGAACAGTG ACCAAGACGA GTTCCTAGGT GTCAATGATG     120

CTTCCATGTT CTACGCTGAT TTCCCTCCTC TCCCTGATTT CCCTTGCATG TCATCATCAT     180

CATCTTCATC TTCAGCAACA CCACTTCCCG TGAAGACCAT GACATGTTCC ACCACCACCA     240

CCACTTCCTC TTCTTCCTCT TCCTCTTCTT GGGCCATGTT GAAGTCAGAT GCTGAGGAAG     300

ATGCAGAGAA AAACCATTGC AACCGATACA TGCATGACCA ACTTGATGCA ACTTTGTCTT     360

CCACCGCTTC CATGGAGATT TCTCAACAGC AAAACCCTGA TCCTGGCCTT GGTGGCACTG     420

TTGGAGAGTG CATGGATGAT GTTATGGACA CTTTTGGTTA CATGGAGCTT TTGGAGGCCA     480

ATGATTTCTT TGACCCTGCC TCTATCTTTC AGAACGAGGG TAACGAAAAC CCTTTAGAGG     540

AGTTTGGCAC ACTGGAGGAG CATGTGCCGT TCATGAAGA GCAACATGCA ATGGTGTTGC     600

ATCAGCAAGG GCAAGCAGAA GAGAAGGATC ATCAGGTTCC TTTTTGTGAA AGATCCAAG     660

GAGATGAAGA AGGTGGTGAT GGTGTTGGAG TAGATGATGA GATGAGTAAT GTGTTCTTGG     720

AGTGGCTTAA GTCTAACAAG GATAGTGTCT CAGCTAATGA CTTGAGGAAT GTGAAGCTCA     780

AGAAGGCGAC ACTCGAAAGC GCGGCGAGGC GGCTAGGGGG AGGAAAAGAA GCCATGAAGC     840

AGTTGCTGAA GCTGATTCTT GAGTGGGTTC AAACCAGCCA TCTTCAGAAT AAGCGCCGAA     900

AGGAAAATAA TGGTAGTAGT ATTAGCAGTG TACTTCAGGC ACAGTTTCAG GATCCTAGTG     960

GCCAGAACAA CAACCAGAAT ACACAAAGTG GTTCATTTGC ACCAGAATCA AACACTTGTT    1020
```

-continued

```
TCAACAACCA AACACCACGG TTGAGTTCTC AAACTTTTGC AACAGATCAG GCTCTTCTCA      1080

TGGTGCCTCC ACAGCAATTT CCACAACCCA TGGTTGGGTA TGTGGGTGAC CCTTACACTA      1140

GTGGTGCTGC TTCAAATAAC ATATCAGCCA CTCATAACCA TAACAACAGC AACCCTTATC      1200

AACCTGGTGC AGAACAATAC CACATGTTGG AGTCAGCACA TTCATGGCCA CATTCTCTGT      1260

TCAATGTTGC TTCTAACTAT AGTCAGTCTT TTGGGGACAA TAATGGTCTT AACCCACATG      1320

GGGGTTTCGG TGGTGGAGGC TATGGCAATA ACCACTACCC TTATCAGTTT TTTCATGGCC      1380

CTGGTGATAG GTTGATGAGG TTGGGGCCCT CCGCGACGAA GGAAGCGAGG AAGAAGAGAA      1440

TGGCAAGGCA AAGAAGGTTT CTGTCTCATC ACAGGCATCA TAGTGGTAAT CACCACAATC      1500

AAGAGTCTGA CCCTCATGCA AGAATGGGGG GTGATAATTG CAACACTGCT TTGGCTGCAC      1560

CTCATCACGC AAATCCTTCA GCCAATTGGA TGTACTGGCA AGCTATGATT GGCGGCGCGG      1620

CAGGTCCTTT GGCTCCGGTG ATTCCGGCCG AGCCGCCGGT GGTACAACCG GTCGTGGACC      1680

GGTCGGCCAT GCAGACACAG AATTGTCCTC CTAATCTAAT TGCATCAGAT AGGAGACAGG      1740

GTTGGAAGCC TGAAGAGAAC TTGAGGTTCC TTCTGCAGAA GGTGTTGAAA CAAAGCGATG      1800

TTGGAAGTTT GGGGAGAATA GTTTTGCCAA AAAAAGAGGC AGAAACCCAT TGCCAGAGC      1860

TGGAGGCAAG AGATGGAATT TCCATAACAA TGGAAGACAT TGGAACTTCA CGTGTTTGGA      1920

ACATGCGCTA TAGATACTGG CCGAACAACA AAAGCAGAAT GTATTTGCTC GAGAACACTG      1980

GTGACTTTGT GAGAGCCAAT GGACTCCAAG AGGGAGATTT CATAGTGATA TACTCAGATG      2040

TGAAGTGTGG CAAATATATG ATAAGAGGAG TGAAAGTGAG GCAACAAGGT GTGAAACCAG      2100

AGACCAAGAA AGCAGGAAAA TCGCAGAAAA ACCAGCATGG GACAGGGACT AATGCATCAA      2160

GTACAGCTGG TACTGCTGCT AATAATGGCA CGTCATCGTC ACCGAAAACC AAATCTGAAA      2220

AAAGTAGTAA ATTAATATAA TATATAGTAT ATGTATGTAC AATATATATT ATGGCATATA      2280

TAATAAAATA AGAGACTCTC AAGTCTGAAC ACGGTGCTCA CATATAATGT TGTGAAGTTT      2340

GAGCATGCCC TGCAATGGAG GCTGTCAAGG ATTTGTATAA CAGTATTTTG GGTAATATTT      2400

CTTTTAGTAG TTTATTTTGC GATTGTTATT AAAAAAAAAA AAAAAAAAAC TCGA            2454
```

(2) INFORMATION FOR SEQ ID NO: 13:

(i) SEQUENCE CHARACTERISTICS:
        (A) LENGTH: 734 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 13:

```
Met Glu Asp Glu His Thr Leu Ala Val Ala Glu Arg Glu Met Trp Leu
1               5                  10                  15

Asn Ser Asp Gln Asp Glu Phe Leu Gly Val Asn Asp Ala Ser Met Phe
            20                  25                  30

Tyr Ala Asp Phe Pro Pro Leu Pro Asp Phe Pro Cys Met Ser Ser Ser
        35                  40                  45

Ser Ser Ser Ser Ser Ala Thr Pro Leu Pro Val Lys Thr Met Thr Cys
    50                  55                  60

Ser Thr Thr Thr Thr Thr Ser Ser Ser Ser Ser Ser Ser Ser Trp Ala
65                  70                  75                  80

Met Leu Lys Ser Asp Ala Glu Glu Asp Ala Glu Lys Asn His Cys Asn
                85                  90                  95
```

-continued

```
Arg Tyr Met His Asp Gln Leu Asp Ala Thr Leu Ser Ser Thr Ala Ser
            100                 105                 110

Met Glu Ile Ser Gln Gln Gln Asn Pro Asp Pro Gly Leu Gly Gly Thr
        115                 120                 125

Val Gly Glu Cys Met Asp Asp Val Met Asp Thr Phe Gly Tyr Met Glu
    130                 135                 140

Leu Leu Glu Ala Asn Asp Phe Phe Asp Pro Ala Ser Ile Phe Gln Asn
145                 150                 155                 160

Glu Gly Asn Glu Asn Pro Leu Glu Glu Phe Gly Thr Leu Glu Glu His
                165                 170                 175

Val Pro Phe His Glu Glu Gln His Ala Met Val Leu His Gln Gln Gly
            180                 185                 190

Gln Ala Glu Glu Lys Asp His Gln Val Pro Phe Cys Glu Glu Ile Gln
        195                 200                 205

Gly Asp Glu Glu Gly Gly Asp Gly Val Gly Val Asp Asp Glu Met Ser
    210                 215                 220

Asn Val Phe Leu Glu Trp Leu Lys Ser Asn Lys Asp Ser Val Ser Ala
225                 230                 235                 240

Asn Asp Leu Arg Asn Val Lys Leu Lys Lys Ala Thr Leu Glu Ser Ala
                245                 250                 255

Ala Arg Arg Leu Gly Gly Lys Glu Ala Met Lys Gln Leu Leu Lys
            260                 265                 270

Leu Ile Leu Glu Trp Val Gln Thr Ser His Leu Gln Asn Lys Arg Arg
        275                 280                 285

Lys Glu Asn Asn Gly Ser Ser Ile Ser Ser Val Leu Gln Ala Gln Phe
    290                 295                 300

Gln Asp Pro Ser Gly Gln Asn Asn Gln Asn Thr Gln Ser Gly Ser
305                 310                 315                 320

Phe Ala Pro Glu Ser Asn Thr Cys Phe Asn Asn Gln Thr Pro Arg Leu
                325                 330                 335

Ser Ser Gln Thr Phe Ala Thr Asp Gln Ala Leu Leu Met Val Pro Pro
            340                 345                 350

Gln Gln Phe Pro Gln Pro Met Val Gly Tyr Val Gly Asp Pro Tyr Thr
        355                 360                 365

Ser Gly Ala Ala Ser Asn Asn Ile Ser Ala Thr His Asn His Asn Asn
    370                 375                 380

Ser Asn Pro Tyr Gln Pro Gly Ala Glu Gln Tyr His Met Leu Glu Ser
385                 390                 395                 400

Ala His Ser Trp Pro His Ser Leu Phe Asn Val Ala Ser Asn Tyr Ser
                405                 410                 415

Gln Ser Phe Gly Asp Asn Asn Gly Leu Asn Pro His Gly Gly Phe Gly
            420                 425                 430

Gly Gly Gly Tyr Gly Asn Asn His Tyr Pro Tyr Gln Phe Phe His Gly
        435                 440                 445

Pro Gly Asp Arg Leu Met Arg Leu Gly Pro Ser Ala Thr Lys Glu Ala
    450                 455                 460

Arg Lys Lys Arg Met Ala Arg Gln Arg Arg Phe Leu Ser His His Arg
465                 470                 475                 480

His His Ser Gly Asn His His Asn Gln Glu Ser Asp Pro His Ala Arg
                485                 490                 495

Met Gly Gly Asp Asn Cys Asn Thr Ala Leu Ala Ala Pro His His Ala
            500                 505                 510
```

-continued

```
Asn Pro Ser Ala Asn Trp Met Tyr Trp Gln Ala Met Ile Gly Gly Ala
            515                 520                 525
Ala Gly Pro Leu Ala Pro Val Ile Pro Ala Glu Pro Pro Val Val Gln
        530                 535                 540
Pro Val Val Asp Arg Ser Ala Met Gln Thr Gln Asn Cys Pro Pro Asn
545                 550                 555                 560
Leu Ile Ala Ser Asp Arg Arg Gln Gly Trp Lys Pro Glu Lys Asn Leu
                565                 570                 575
Arg Phe Leu Leu Gln Lys Val Leu Lys Gln Ser Asp Val Gly Ser Leu
            580                 585                 590
Gly Arg Ile Val Leu Pro Lys Lys Glu Ala Glu Thr His Leu Pro Glu
        595                 600                 605
Leu Glu Ala Arg Asp Gly Ile Ser Ile Thr Met Glu Asp Ile Gly Thr
    610                 615                 620
Ser Arg Val Trp Asn Met Arg Tyr Arg Tyr Trp Pro Asn Asn Lys Ser
625                 630                 635                 640
Arg Met Tyr Leu Leu Glu Asn Thr Gly Asp Phe Val Arg Ala Asn Gly
                645                 650                 655
Leu Gln Glu Gly Asp Phe Ile Val Ile Tyr Ser Asp Val Lys Cys Gly
            660                 665                 670
Lys Tyr Met Ile Arg Gly Val Lys Val Arg Gln Gly Val Lys Pro
        675                 680                 685
Glu Thr Lys Lys Ala Gly Lys Ser Gln Lys Asn Gln His Gly Thr Gly
    690                 695                 700
Thr Asn Ala Ser Ser Thr Ala Gly Thr Ala Ala Asn Asn Gly Thr Ser
705                 710                 715                 720
Ser Ser Pro Lys Thr Lys Ser Glu Lys Ser Ser Lys Leu Ile
                725                 730
```

(2) INFORMATION FOR SEQ ID NO: 14:

(i) SEQUENCE CHARACTERISTICS:
        (A) LENGTH: 750 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 14:

```
Met Glu Cys Glu Val Lys Leu Lys Gly Gly Asp Leu His Ala Glu Gly
1               5                   10                  15
Val Thr Glu Thr Asn Ala Val Gly Phe Asp Ala Met Glu Asp Glu Gln
            20                  25                  30
Thr Leu Thr Val Ala Glu Arg Glu Met Trp Leu Asn Ser Asp Gln Asp
        35                  40                  45
Glu Phe Leu Gly Val Asn Glu Ala Ser Met Phe Tyr Ala Asn Phe Pro
    50                  55                  60
Pro Leu Pro Asp Phe Pro Cys Thr Ser Ser Ser Ser Ser Ser Ser Ser
65                  70                  75                  80
Ala Ala Pro Leu Pro Leu Lys Thr Thr Thr Cys Ser Thr Thr Thr Thr
                85                  90                  95
Ala Thr Thr Ala Thr Ser Ser Ser Ser Ser Ser Ser Trp Ala Val
            100                 105                 110
Leu Lys Ser Asp Val Glu Glu Asp Val Glu Lys Asn His Cys Asn
        115                 120                 125
```

-continued

```
Gly Ser Met Gln Asp Gln Phe Asp Ala Thr Ala Leu Ser Ser Thr Ala
    130                 135                 140

Ser Met Glu Ile Ser Gln Gln Asn Pro Asp Pro Gly Leu Gly Gly
145                 150                 155                 160

Ser Val Gly Glu Cys Met Glu Asp Val Met Asp Thr Phe Gly Tyr Met
                165                 170                 175

Glu Leu Leu Glu Ala Asn Asp Phe Phe Asp Pro Ala Ser Ile Phe Gln
            180                 185                 190

Asn Glu Glu Ser Glu Asp Pro Leu Ile Glu Phe Gly Val Leu Glu Glu
                195                 200                 205

Gln Val Ser Leu Gln Glu Gln His Glu Met Val His Gln Gln Glu
    210                 215                 220

Asn Thr Glu Glu Asp Arg Lys Val Pro Val Cys Glu Val Ile Lys Gly
225                 230                 235                 240

Glu Glu Glu Gly Gly Gly Gly Gly Gly Arg Val Val Asp Asp Glu
                245                 250                 255

Met Ser Asn Val Phe Leu Glu Trp Ser Lys Ser Asn Lys Asp Ser Val
            260                 265                 270

Ser Ala Asn Asp Leu Arg Asn Val Lys Leu Lys Lys Ala Thr Ile Glu
    275                 280                 285

Ser Ala Ala Lys Arg Leu Gly Gly Gly Lys Glu Ala Met Lys Gln Leu
    290                 295                 300

Leu Lys Leu Ile Leu Glu Trp Val Gln Thr Ser His Leu Gln Asn Lys
305                 310                 315                 320

Arg Arg Lys Glu Asn Gly Ser Asn Ala Leu Gln Ala Thr Phe Gln Asp
                325                 330                 335

Pro Ser Ala Gln Thr Lys Glu Asn Ala His Thr Ser Gly Ser Phe Ala
            340                 345                 350

Pro Glu Ser Asn Ser Cys Phe Asn Asn Gln Thr Pro Trp Leu Asn Pro
        355                 360                 365

Gln Thr Phe Gly Thr Asp Gln Ala Pro Val Met Val Pro Ser Gln Pro
    370                 375                 380

Tyr Ser Gln Pro Val Ala Gly Tyr Val Gly Asp Pro Tyr Thr Ser Gly
385                 390                 395                 400

Ser Ala Pro Asn Asn Ile Thr Val Asn His Asn His Asn Asn Asn Pro
                405                 410                 415

Tyr Gln Pro Gly Thr Asp Gln Tyr His Met Leu Glu Ser Ala His Ser
            420                 425                 430

Trp Pro His Ser Gln Phe Asn Val Ala Ser His Tyr Ser Gln Ser Tyr
        435                 440                 445

Gly Glu Asn Gly Leu Phe Thr His Gly Gly Phe Gly Gly Tyr Ala Ile
    450                 455                 460

Thr Arg Tyr Pro Tyr Gln Phe Phe His Gly Pro Gly Asp Arg Leu Met
465                 470                 475                 480

Arg Leu Gly Pro Ser Ala Thr Lys Glu Ala Arg Lys Lys Arg Met Ala
                485                 490                 495

Arg Gln Arg Lys Phe Leu Ser His Arg Asn Gln Asn Gly Asn His
            500                 505                 510

Leu Gln Asn Gln Gly Ser Asp Pro His Ala Arg Leu Gly Asn Asp Asn
        515                 520                 525

Cys Thr Thr Gly Leu Val Ala Pro His Gln Pro Asn Ser Ala Ala Ala
    530                 535                 540

Asn Trp Met Tyr Trp Gln Ala Met Thr Gly Gly Pro Ala Gly Pro Leu
```

-continued

```
545                 550                 555                 560

Ala Pro Val Val Pro Ala Asp Pro Leu Ala Gly Gln Thr Val Val Asp
            565                 570                 575

Arg Thr Thr Met His Thr Gln Asn Ser His Gln Asn Arg Ala Ala Ser
            580                 585                 590

Asp Arg Arg Gln Gly Trp Lys Pro Glu Lys Asn Val Arg Phe Leu Gly
        595                 600                 605

Gln Lys Val Leu Lys Gln Ser Asp Val Gly Lys Leu Gly Arg Ile Val
        610                 615                 620

Leu Pro Lys Lys Glu Ala Glu Thr His Leu Pro Glu Leu Glu Ala Arg
625                 630                 635                 640

Asp Gly Ile Ser Ile Thr Met Glu Asp Ile Gly Thr Ser Arg Val Trp
                645                 650                 655

Asn Met Arg Tyr Arg Tyr Trp Pro Asn Asn Lys Ser Arg Met Tyr Met
                660                 665                 670

Leu Glu Asn Thr Gly Asp Phe Val Arg Ala Asn Gly Leu Gln Glu Gly
            675                 680                 685

Asp Phe Ile Val Ile Tyr Ser Asp Val Lys Cys Gly Lys Tyr Met Ile
        690                 695                 700

Arg Gly Val Lys Val Arg Gln Gln Gly Val Lys Pro Glu Thr Lys Pro
705                 710                 715                 720

Ala Gly Lys Ser Gln Lys Thr Thr Gly Thr Asn Ala Ser Tyr Thr
                725                 730                 735

Ala Gly Thr Ala Ala Asn Asn Gly Met Ser Ser His Arg Asn
            740                 745                 750
```

US 6,252,137 B1

SOYBEAN HOMOLOG OF SEED-SPECIFIC TRANSCRIPTION ACTIVATOR FROM *PHASEOLUS VULGARIS*

This is a continuation-in-part of provisional application Ser. No. 60/065,459 filed Nov. 12, 1997, now abandoned.

FIELD OF THE INVENTION

This invention is in the field of plant molecular biology. More specifically, this invention pertains to nucleic acid fragments encoding transcirption activator proteins involved in regulation of gene expression in seeds.

BACKGROUND OF THE INVENTION

Gene expression levels are influenced by the interactions of transcription factors with proteins that are present in general transcription complexes. Transcription factors generally have an activation domain and a DNA binding domain. In addition, other non-DNA binding proteins known as coactivators interact with transcription factors and transcription complex proteins to further stimulate transcription. The proteins PvAlf of *Phaseolus vulgaris* (Bobb et al. (1995) *Plant Journal* 8:101–113), ABI3 of *Arabidopsis thaliana* (Giraudat et al. (1992) *Plant Cell* 4:1251–1261), and Vp1 of maize (McCarty et al. (1991) *Cell* 66:895–905) and rice (Hattori et al. (1994) *Plant Molecular Biology* 24:805–810) are related proteins that are involved in the regulation of transcription. They have been called transcription factors, though it is unclear whether they actually can bind to DNA. They may bind to DNA in conjunction with another protein, or may actually be a coactivator type of regulator. In any case, these related proteins are stimulators of transcription. Due to the uncertainty in classification, we refer to these proteins as transcription activators, which could either be transcription factors or transcription coactivators.

PvAlf is expressed specifically during seed development. The highest levels of expression of PvAlf mRNA are at the time when seed storage protein expression begins. In transient assays in bean cotyledons, PvAlf positively regulated the expression of the phaseolin and phytohemagglutinin promoters, the promoters of two abundantly expressed seed storage protein genes (Bobb et al., (1995) *Plant Journal* 8:101–113). The activation response was shown to be mediated through sequences that are conserved in these and other seed storage protein gene promoters, called the Ry-repeats, as well as an associated CCAC sequence (Bobb et al. (1997) *Nucleic Acids Res.* 25:641–647). The N-terminal 243 amino acids of PvAlf were shown in transient assays in bean cotyledons to function as an activation domain, when fused to the DNA binding domain of the yeast Gal4 transcription factor (Bobb et al. (1995) *Plant Journal* 8:101–113).

The PvAlf-related ABI3 gene product of Arabidopsis is also involved in the regulation of seed storage protein genes. Mutants in the ABI3 gene cause a reduction or loss of expression of the 2S and 12S seed storage proteins (Nambara et al. (1994) *Plant Cell Physiol.* 35:509–513; Parcy et al. (1994) *Plant Cell* 6:1567–1582). Mutants in the related Vp1 gene of maize also cause reduction in seed storage protein expression (Kriz et al (1990) *Plant Physiol.* 92:538–542). In transient assays in maize protoplasts, Vp1 activated the maize Em promoter, the promoter from a gene expressed during embryo development (McCarty et al. (1991) *Cell* 66:895–905). The activation domain of Vp1 was localized to the N-terminal 121 amino acids in Gal4 fusion experiments using transient assays (McCarty et al. (1991) *Cell* 66:895–905). Like PvAlf, ABI3 and Vp1 expression is specific to seed development.

To date, no PvAlf, ABI3 or VP1 homologs have been reported in *Glycine max*.

SUMMARY OF THE INVENTION

The instant invention relates to isolated nucleic acid fragments encoding a plant protein involved in regulation of gene expression. More particularly, this invention concerns isolated nucleic acid fragments encoding a soybean homolog of the *Phaseolus vulgaris* PvAlf transcription activator. In addition, this invention relates to nucleic acid fragments that are complementary to nucleic acid fragments encoding the *Phaseolus vulgaris* PvAlf transcription activator.

In another embodiment, the instant invention relates to a chimeric gene that comprises a nucleic acid fragment encoding a soybean homolog of the *Phaseolus vulgaris* PvAlf transcription activator, or to a chimeric gene that comprises a nucleic acid fragment that is complementary to a nucleic acid fragment encoding a soybean homolog of the *Phaseolus vulgaris* PvAlf transcription activator, the nucleic acid fragment operably linked to suitable regulatory sequences, wherein expression of the chimeric gene results in production of levels of the encoded protein in transformed host cells that are altered (i.e., increased or decreased) relative to the levels produced in untransformed host cells.

In a further embodiment, the instant invention concerns a transformed host cell comprising in its genome a chimeric gene comprising a nucleic acid fragment encoding a soybean homolog of the *Phaseolus vulgaris* PvAlf transcription activator or a chimeric gene comprising a nucleic acid fragment that is complementary to the nucleic acid fragment encoding soybean homolog of the *Phaseolus vulgaris* PvAlf transcription activator, the chimeric gene operably linked to suitable regulatory sequences. Expression of the chimeric gene results in production of altered levels of protein encoded by the operably linked nucleic acid fragment in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a plant homolog of the *Phaseolus vulgaris* PvAlf transcription activator in a transformed host cell comprising: a) transforming a host cell with a chimeric gene comprising a nucleic acid fragment encoding a soybean homolog of the *Phaseolus vulgaris* PvAlf transcription activator or a chimeric gene that comprises a nucleic acid fragment that is complementary to the nucleic acid fragment encoding a soybean homolog of the *Phaseolus vulgaris* PvAlf transcription activator; and b) growing the transformed host cell under conditions that are suitable for expression of the chimeric gene wherein expression of the chimeric gene results in production of altered levels of the plant homolog of the *Phaseolus vulgaris* PvAlf transcription activator in the transformed host cell.

An additional embodiment of the instant invention concerns a method for obtaining a nucleic acid fragment encoding all or substantially all of an amino acid sequence encoding a platnt homolog of the *Phaseolus vulgaris* PvAlf transcription activator.

BRIEF DESCRIPTION OF THE DRAWINGS AND SEQUENCE DESCRIPTIONS

The invention can be more fully understood from the following detailed description and the accompanying drawing and Sequence Listing which form a part of this application.

FIG. 1 shows a comparison of the amino acid sequences of the *Phaseolus vulgaris* PvAlf transcriptional activator (pvalf.PRO) and the instant *Glycine max* homologs of PvAlf referred to herein as clones Sbs20 (sbs20.PRO), Sbs12 (sbs12.PRO), Sb8a (sb8a.PRO) and ses8w.pk0003.d6 (03d6.PRO). Shading indicates conserved amino acid residues.

The following sequence descriptions and sequence listings attached hereto comply with the rules governing nucleotide and/or amino acid sequence disclosures in patent applications as set forth in 37 C.F.R. §1.821–1.825.

SEQ ID NO:1 is the nucleotide sequence comprising part of the cDNA insert in clone s2.06c04 encoding a portion of a soybean homolog of the *Phaseolus vulgaris* PvAlf transcriptional activator.

SEQ ID NO:2 is the gene-specific primer PH419 used to isolate clone Sbs20 encoding the N-terminal portion of a a soybean homolog of the *Phaseolus vulgaris* PvAlf transcriptional activator.

SEQ ID NO:3 is the vector-specific primer T3 used to isolate clone Sbs20 encoding the N-terminal portion of a a soybean homolog of the *Phaseolus vulgaris* PvAlf transcriptional activator.

SEQ ID NO:4 is the gene-specific primer PH422 used to isolate clone Sbs12 encoding the C-terminal portion of a a soybean homolog of the *Phaseolus vulgaris* PvAlf transcriptional activator.

SEQ ID NO:5 is the vector-specific primer T7 used to isolate clone Sbs 12 encoding the C-terminal portion of a a soybean homolog of the *Phaseolus vulgaris* PvAlf transcriptional activator.

SEQ ID NO:6 is the nucleotide sequence comprising the DNA insert in clone Sbs20 encoding the N-terminal portion of a soybean homolog of the *Phaseolus vulgaris* PvAlf transcriptional activator.

SEQ ID NO:7 is the deduced amino acid sequence of the N-terminal portion of a soybean homolog of the *Phaseolus vulgaris* PvAlf transcriptional activator derived from the nucleotide sequence of SEQ ID NO:6.

SEQ ID NO:8 is the nucleotide sequence comprising the DNA insert in clone Sbs12 encoding the C-terminal portion of a soybean homolog of the *Phaseolus vulgaris* PvAlf transcriptional activator.

SEQ ID NO:9 is the deduced amino acid sequence of the C-terminal portion of a soybean homolog of the *Phaseolus vulgaris* PvAlf transcriptional activator derived from the nucleotide sequence of SEQ ID NO:8.

SEQ ID NO:10 is the nucleotide sequence comprising the DNA insert in clone Sb8a encoding the entire amino acid sequence of a soybean homolog of the *Phaseolus vulgaris* PvAlf transcriptional activator.

SEQ ID NO:11 is the deduced amino acid sequence of the entire coding region of a soybean homolog of the *Phaseolus vulgaris* PvAlf transcriptional activator derived from the nucleotide sequence of SEQ ID NO: 10.

SEQ ID NO: 12 is the nucleotide sequence comprising part of the cDNA insert in clone ses8w.pk0003.d6 encoding the entire amino acid sequence of a soybean homolog of the *Phaseolus vulgaris* PvAlf transcriptional activator.

SEQ ID NO:13 is the deduced amino acid sequence of the entire coding region of a soybean homolog of the *Phaseolus vulgaris* PvAlf transcriptional activator derived from the nucleotide sequence of SEQ ID NO:12.

SEQ ID NO: 14 is the amino acid sequence encoding the *Phaseolus vulgaris* PvAlf transcriptional activator having GenBank accession No. U28645.

The Sequence Listing contains the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

The amino acid sequence similarity between the instant soybean protein and the *Phaseolus vulgaris* PvAlf transcription activator indicates that the soybean homolog may function as a transcription activator. The soybean protein may be used to enhance gene expression of those genes whose promoters are normally targeted by the transcription activators that the soybean homologs of PvAlf normally interact with. The soybean gene may be used to reduce expression of specific genes whose promoters are normally regulated by the soybean homolog of PvAlf, using antisense or co-suppression technology.

Alternatively, the soybean homolog of the *Phaseolus vulgaris* PvAlf transcription activator, or a portion thereof, can be targeted to a novel promoter region by the addition of either a DNA binding domain or a protein-protein interaction domain. The instant soybean Alf protein, or a portion thereof such as the activation domain, can be fused to a very defined DNA-binding domain, such as, but not limited to, a bacterial lexA DNA binding domain, a yeast Gal4 DNA-binding domain or a DNA binding domain from a plant transcription factor. For example, it has also been shown that targeting the yeast transcriptional adaptor protein ADA2 to a promoter by fusing it to a heterologous DNA-binding domain leads to transcriptional activation in yeast (Silverman et al. (1994) *Proc. Natl. Acad. Sci. USA* 91:11665–11668). On the other hand, a synthetic promoter can be designed to contain multiple copies of a target site which is necessary for the specific binding by either the lexA, Gal4 or plant DNA binding domain. By using this approach, the *Glycine max* homolog of the *Phaseolus vulgaris* PvAlf or its activation domain can be specifically targeted to the engineered synthetic promoter, thus leading to a higher level of gene expression.

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a coding sequence which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar nucleic acid sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are 80% identical to the coding sequence of the nucleic acid fragments reported herein. More preferred nucleic acid fragments are 90% identical to the coding sequence of the nucleic acid fragments reported herein. Most preferred are nucleic acid fragments that are 95% identical to the coding sequence of the nucleic acid fragments reported herein. The percent identity used herein, can be precisely determined by the DNASTAR protein alignment protocol using the Jotun Hein algorithm (Hein, J. J. (1990) *Methods in Enzymology* 183:626–645). Default parameters for the Jotun-Hein method for multiple alignments are: GAP PENALTY=11, GAP LENGTH PENALTY=3; for pairwise alignments KTUPLE 2.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the soybean homolog of the *Phaseolus vulgaris* PvAlf transcription activator as set forth in SEQ ID NO:2, 4, 6 and 8. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that encodes a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be a native element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed MRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript. Alternatively, the RNA transcript may be an RNA sequence derived from posttranscriptional processing of the primary transcript; this is referred to as the mature RNA. "Messenger RNA" (mRNA) refers to the RNA that is without introns and that can be translated into protein by the cell. "cDNA" refers to a double-stranded DNA that is complementary to and derived from mRNA. "Sense" RNA refers to an RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

This invention relates to a plant cDNA with homology to the *Phaseolus vulgaris* PvAlf transcription activator. A soybean (*Glycine max*) homolog of the *Phaseolus vulgaris* PvAlf transcription activator was isolated and identified by comparison of random plant EST sequences to the GenBank database using the BLAST algorithms well known to those skilled in the art. This initial EST (s2.06c04), when compared with the published PvAlf sequence, appeared to represent only a portion of a soybean homolog of the PvAlf gene, lacking nucleotide sequences sufficient to encode both the N- and C-terminal ends. The EST sequence was then used to design several gene-specific PCR primers. In conjunction with several vector primers, the gene-specific primers were used to obtain PCR fragments comprising nucleotide sequences encoding N- and C-terminal portions of a soybean homolog of the PvAlf gene. Clones encoding the N- and C-terminal ends of a soybean homolog of the PvAlf gene were designated Sbs20 and Sbs 12, respectively. Subsequently, a single cDNA clone, designated Sb8a and containing a complete coding region of a soybean homolog of the PvAlf gene soyAlf gene, was obtined by conventional library screening methods using the cDNA insert from clone Sbs20 as a probe. Continued screening of soybean EST sequences yielded an additonal cDNA clone, ses8w.pk0003.d6, representing a coding sequence of a complete soybean homolog of the PvAlf gene. Comparison of all of the instant EST and cDNA clone sequences indicates that these sequences represent at least three unique but highly related genes or alleles encoding homologs of the *Phaseolus vulgaris* PvAlf transcription activator. Identification and utilization of these PvAlf homologs may provide a means for regulating gene expression in plants.

The nucleic acid fragments of the instant invention may be used to isolate cDNAs and genes encoding other homologs of the *Phaseolus vulgaris* PvAlf transcription activator from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other plant homologs of PvAlf, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency. Genomic fragments can be isolated that include the promoter region that directs expression of the soybean homolog of the *Phaseolus vulgaris* PvAlf transcription activator protein. This promoter may be prepared as a DNA fragment including regulatory elements with or without the untranslated leader and used in expression of other coding regions or for co-suppression.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed soybean homolog of PvAlf is present at higher or lower levels than normal or in cell types or developmental stages in which it is not normally found. This would have the effect of altering the level of a soybean homolog of the PvAlf gene in those cells.

Overexpression of the soybean homolog of the *Phaseolus vulgaris* PvAlf transcription activator may be accomplished by first constructing a chimeric gene in which the coding region is operably linked to a promoter capable of directing expression of a gene in the desired tissues at the desired stage of development. For reasons of convenience, the chimeric gene may comprise a promoter sequence and translation leader sequence derived from the same gene. A 3' non-coding sequence encoding a transcription termination signal may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J* 4:2411–2418; De Almeida et al., (1989) *Mol Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications, it may be desirable to reduce or eliminate expression of the genes encoding homologs of the *Phaseolus vulgaris* PvAlf transcription activator in soybean. In order to accomplish this, chimeric genes designed for co-suppression of soybean homologs of PvAlf can be constructed by linking the genes or gene fragments encoding the the soybean homolog of the *Phaseolus vulgaris* PvAlf transcription activator to plant promoter sequences. Alternatively, chimeric genes designed to express antisense RNA for all or part of the instant nucleic acid fragments can be constructed by linking the genes or gene fragments in reverse orientation to plant promoter sequences. Either the co-suppression or antisense chimeric genes could be introduced into plants via transformation wherein expression of the corresponding endogenous genes are reduced or eliminated.

The instant soybean homologs of the *Phaseolus vulgaris* PvAlf transcription activator (or portions thereof) may be produced in heterologous host cells, particularly in the cells of microbial hosts, and can be used to prepare antibodies to the soybean homolog of PvAlf by methods well known to those skilled in the art. The antibodies are useful for detecting the soybean homolog of PvAlf in situ in cells or in vitro in cell extracts. Preferred heterologous host cells for production of the instant soybean homologs of the *Phaseolus vulgaris* PvAlf transcription activator are microbial hosts. Microbial expression systems and expression vectors containing regulatory sequences that direct high level expression of foreign proteins are well known to those skilled in the art. Any of these could be used to construct chimeric genes for production of the instant soybean homologs of the *Phaseolus vulgaris* PvAlf transcription activator. These chimeric genes could then be introduced into appropriate microorganisms via transformation to provide high level expression of the soybean homolog of PvAlf. An example of a vector for high level expression of the instant soybean homologs of the *Phaseolus vulgaris* PvAlf transcription activator in a bacterial host is provided (Example 8).

All or a portion of the nucleic acid fragments of the instant invention may also be used as probes for genetically and physically mapping the genes that they are a part of, and as markers for traits linked to expression of plant homologs of the *Phaseolus vulgaris* PvAlf transcription activator. Such information may be useful in plant breeding in order to develop lines with desired phenotypes.

For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am.J Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for plant homologs of the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant Alf gene. Alternatively, the soyAlf gene may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous Alf gene can be identified and obtained. This mutant plant can then be used to determine or confirm the natural functon of the plant Alf gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones

Several cDNA libraries representing mRNAs obtained from various developmental stages of soybean embryos were prepared in Uni-ZAP™ XR vector according to the manufacturer's protocol (Stratagene Cloning Systems, La Jolla, Calif.). The characteristics of these libaries and the names of clones containing sequences of soybean homologs of PvAlf are described in the table below:

TABLE 1 cDNA Libraries from Soybean Tissues

| Library | Tissue | Clone |
| --- | --- | --- |
| se3 | Soybean Embryo 13 Days After Flowering | Sbs20<br>Sbs12 |
| s2 | Soybean Embryo 17 Days After Flowering | s2.06c04 |
| se5 | Soybean Embryo 21 Days After Flowering | Sb8a |
| ses8w | Mature Soybean Embryo 8 Weeks After Subculture | ses8w.pk0003.d6 |

Conversion of the Uni-ZAP™ XR libraries into plasmid libraries was accomplished according to the protocol provided by Stratagene. Upon conversion, cDNA inserts were contained in the plasmid vector pBluescript. For screening of partial cDNA sequences, cDNA inserts from randomly picked bacterial colonies containing recombinant pBluescript plasmids were amplified via polymerase chain reaction using primers specific for vector sequences flanking the inserted cDNA sequences. Amplified insert DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification and Characterization of a Soybean EST Encoding a Portion of a Homolog of the Phaseolus vulgaris PvAlf Transcription Activator An EST encoding a homolog of the *Phaseolus vulgaris* PvAlf transcription activator was identified by conducting BLAST (Basic Local Alignment Search Tool; Altschul, S. F., et al., (1993) *J Mol. Biol*. 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The EST sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequence from clone s2.06c04 revealed similarity of the protein encoded by the cDNA to the *Phaseolus vulgaris* PvAlf transcription activator (GenBank Accession No. U28645; pLog=32.05). SEQ ID NO:1 shows the nucleotide sequence of the EST. BLAST scores and probabilities indicated that the EST derived from clone s2.06c04 encoded at least an indentifiable portion of a soybean homolog of the *Phaseolus vulgaris* PvAlf transcription activator. However, comparison of the EST sequence to the complete coding sequence of the *Phaseolus vulgaris* PvAlf transcription activator indicated that the cDNA insert in clone s2.06c04 lacked sufficient nucleic acid sequence information to encode the N- and C-terminal ends of the protein.

Example 3

Isolation of Clones Encoding the N- and C-Terminal Portions of a Soybean Homolog of the Phaseolus vulgaris PvAlf Transcription Activator Several gene specific PCR primers, as well as several vector primers, were designed in order to obtain clones encoding the N- and C-terminal portions of a soybean homolog of the *Phaseolus vulgaris* PvAlf transcription activator. A cDNA encoding the N-terminal portion (Sbs20) was isolated using the gene specific primer PH419 (SEQ ID NO:2) and the vector primer T3 (SEQ ID NO:3). A cDNA encoding the C-terminal portion (Sbs12) was isolated using the gene specific primer PH422 (SEQ ID NO:4) and the vector primer T7 (SEQ ID NO:5). The sequence of the gene specific primer PH419 was based upon the sequence of the *Phaseolus vulgaris* PvALF at positions 236–254. The sequence of the gene specific primer PH422 was based upon the sequence of clone s2.06c04 (SEQ ID NO:1), position 389–410. The template used for these PCR reactions was a cDNA library derived from mRNAs obtained from soybean embryos 13 days after flowering. PCR products were generated as follows. After a 2 minute, 96° C. denaturation step, amplification was carried out for 25 cycles comprising: 94° C. for 1 minute, 55° C. for 1 minute, and 72° C. for 2 min. The resulting PC products were cloned using a TA cloning vector, pCR2000, (Invitrogen, San Diego, Calif.) and the resulting plasmids were transformed into *E. coli* DH5α (GIBCO BRL Products, Gaithersburg, Md.). Bacterial transformants were selected by growth on LB media containing 100 μg/ml ampicillin and were further screened by gel electrophoresis to identify transformants containing DNA inserts. Potential positive clones were sequenced, and two clones, Sbs20 (SEQ ID NO:6) and Sbs12 (SEQ ID NO:8) were identified that contained nucleotide sequences encoding the N- and C-terminal ends of the soybean homolog of the PvAlf protein. The amino acid sequences deduced from the nucleotide sequences comprising SEQ ID NOs:6 and 8 are set forth in SEQ ID NO:7 and 9, respectively.

Example 4

Isolation of a cDNA Clone Encoding an Entire Soybean Homolog of the Phaseolus vulgaris PvAlf Transcription Activator A cDNA library representing mRNAs from soybean embryos approximately twenty-one days after flowering was prepared in Uni-ZAP™ XR vectors according to the manufacturer's protocol (Stratagene Cloning Systems, La Jolla, Calif.). Approximately 40,000 plaques from this library were screened using conventional protocols as recommended by Clontech. The cDNA insert in clone Sbs20 (SEQ ID NO:6) was labeled with $^{32}$p and used to probe the library. In the primary screen, twenty-eight plaque pools were selected as potential positive clones. These pools were then tested by PCR to determine which were likely to contain the complete 5' end of the gene. PCR experiments were carried out as described in Example 3, using primers T3 (SEQ ID NO:3) and PH419 (SEQ ID NO:2). Four plaque pools from the original twenty-eight were selected as those most likely to contain the entire soybean homolog of PvAlf since they contained the 5' end. In order to obtain single phage isolates containing the soybean homolog of PvAlf, these four plaque pools were screened a second time, as described above, again using Sbs20 as a probe. Twenty positive plaques were selected in this secondary screen. Four out of the twenty were shown to contain the complete 5' end of the gene in subsequent PCR tests, carried out as described above. These four isolates were converted into plasmids following the protocol provided by Stratagene. Upon conversion, cDNA inserts were contained in the plasmid vector pBluescript. Following excision of the cDNA from vector, one of the isolated clones (SB8a; SEQ ID NO:10) was found to encode an entire soybean homolog of PvAlf.

Example 5

Identification and Characterization of a Soybean EST Encoding an Entire Soybean Homolog of the *Phaseolus vulgaris* PvAlf Transcription Activator BLASTX searching using the nucleotide sequence from clone ses8w.pk0003.d6 revealed similarity of the protein encoded by the cDNA to the *Phaseolus vulgaris* PvAlf transcription activator (GenBank Accession No. U28645; pLog=41.66). SEQ ID NO:12 shows the nucleotide sequence of the entire soybean cDNA insert; the deduced amino acid sequence is shown in SEQ ID NO:13. The sequence of the entire cDNA insert in clone ses8w.pk0003.d6 was evaluated by BLASTX, yielding even higher pLog values vs. the Phaseolus sequence. Moreover, a BLASTP search using the amino acid sequence shown in SEQ ID NO:13 reconfirmed the identity of this cDNA clone as a soybean homolog of the *Phaseolus vulgaris* PvAlf transcription activator.

Example 6

Expression of Chimeric Genes in Monocot Cells

A chimeric gene comprising a cDNA encoding a soybean homolog of a *Phaseolus vulgaris* PvAlf transcription activator in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is performed in a standard PCR and the amplified DNA is then digested with restriction enzymes NcoI and SmaI and fractionated on an agarose gel. The appropriate band can be excised from the gel and combined with a 4.9 kb NcoI-SmaI fragment of the plasmid pML103.

Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a soybean homolog of a *Phaseolus vulgaris* PvAlf transcription activator, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3O region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 7

Expression of Chimeric Genes in Dicot Cells

A seed-specific expression cassette composed of the promoter and transcription terminator from the gene encoding the p subunit of the seed storage protein phaseolin from the bean *Phaseolus vulgaris* (Doyle et al. (1986) *J Biol. Chem.* 261:9228–9238) can be used for expression of the instant soybean homolog of a *Phaseolus vulgaris* PvAlf transcription activator in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

A nucleic acid fragment encoding a soybean homolog of a *Phaseolus vulgaris* PvAlf transcription activator may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed, and the isolated fragment is inserted into a pUC18 vector carrying the seed expression cassette.

Soybean embroys may then be transformed with the expression vector comprising sequences encoding the soybean homolog of a *Phaseolus vulgaris* PvAlf transcription activator. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A Du Pont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al.(1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the *Phaseolus lunatus* ADA2 homolog and the phaseolin 3' region can be isolated as a restriction fragment. This fragment can then be inserted into a unique restriction site of the vector carrying the marker gene.

To 50 $\mu$L of a 60 mg/mL 1 $\mu$m gold particle suspension is added (in order): 5 $\mu$L DNA (1 $\mu$g/$\mu$L), 20 $\mu$l spermidine (0.1 M), and 50 $\mu$L CaCl$_2$ (2.5 M). The particle preparation is then agitated for three minutes, spun in a microfuge for 10 seconds and the supernatant removed. The DNA-coated particles are then washed once in 400 $\mu$L 70% ethanol and resuspended in 40 $\mu$L of anhydrous ethanol. The DNA/particle suspension can be sonicated three times for one second each. Five $\mu$L of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8

Expression of Chimeric Genes in Microbial Cells

The cDNA encoding the instant soybean homolog of a *Phaseolus vulgaris* PvAlf transcription activator can be inserted into the T7 *E. coli* expression vector pET24d (Novagen). Plasmid DNA containing a cDNA may be appropriately digested to release a nucleic acid fragment encoding the ADA2 protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pET24d is digested, dephosphorylated with alkaline phosphatase (NEB) and deproteinized with phenol/chloroform as decribed above. The prepared vector pET24d and fragment can then be ligated at 16° C. for 15 hours followed by transformation into DH5 electrocompetent cells (GIBCO BRL). Transformants can be selected on agar plates containing 2xYT media and 50 μg/mL kanamycin. Transformants containing the gene are then screened for the correct orientation with respect to pET24d T7 promoter by restriction enzyme analysis. Clones in the correct orientation with respect to the T7 promoter can be transformed into BL21 (DE3) competent cells (Novagen) and selected on 2xYT agar plates containing 50 μg/ml kanamycin. A colony arising from this transformation construct can be grown overnight at 30° C. in 2xYT media with 50 μg/mL kanamycin. The culture is then diluted two fold with fresh media, allowed to re-grow for 1 h, and induced by adding isopropyl-thiogalactopyranoside to 1 mM final concentration. Cells are then harvested by centrifugation after 3 h and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a PvAlf transcription activator homolog, wherein the nucleotide sequence encoding the PvAlf transcription activator homolog and the nucleotide sequence of SEQ ID NO:6, SEQ ID NO:8, SEQ ID NO:10, or SEQ ID NO:12 have at least 80% identity based on the Jotun-Hein alignment method, or
   (b) the complement of the nucleotide sequence encoding tihe PvAlf transcription activator homolog.

2. The polynucleotide of claim 1 wherein the nucleotide sequence encoding the PvAlf transcription activator homolog and the nucleotide sequence of SEQ ID NO:6, SEQ ID NO:8, SEQ ID NO:10, or SEQ ID NO:12 have at least 90% identity based on the Jotun-Hein alignment method.

3. The polynucleotide of claim 1 wherein the nucleotide sequence encoding the PvAlf trascription activator homolog and the nucleotide sequence of SEQ ID NO.6, SEQ ID NO:8, SEQ ID NO:10, or SEQ ID NO:12 have at least 95% identity based on the Jotun-Hein alignment method.

4. The polynucleotide of claim 1 comprising the nucleotide sequence of SEQ ID NO:1, SEQ ID NO:6, SEQ ID NO:8, SEQ ID NO:10, or SEQ ID NO:12.

5. A chimeric gene comprising die polynucleotide of claim 1 operably linked to a regulatory sequence.

6. A. vector comprising die polynucleotide of claim 1.

7. An isolated polynucleotide comprising a nucleotide sequence comprised by the polynucleotide of claim 1 wherein the nucleotide sequence contains 20 to 30 consecutive nucleotides.

8. A method for transforming a cell comprising transforming a cell with the polynucleotide of claim 1.

9. The cell produced by die method of claim 8.

* * * * *